United States Patent
Martinez-Grau

(10) Patent No.: US 9,035,051 B1
(45) Date of Patent: May 19, 2015

(54) GHRELIN O-ACYL TRANSFERASE INHIBITOR

(71) Applicant: Eli Lilly and Company, Indianapolis, IN (US)

(72) Inventor: Maria Angeles Martinez-Grau, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/534,212

(22) Filed: Nov. 6, 2014

(30) Foreign Application Priority Data

Nov. 14, 2013 (EP) ..................................... 13382460

(51) Int. Cl.
*A61K 31/506* (2006.01)
*C07D 401/06* (2006.01)

(52) U.S. Cl.
CPC ............ *A61K 31/506* (2013.01); *C07D 401/06* (2013.01)

(58) Field of Classification Search
CPC ............................ C07D 401/06; A61K 31/506
See application file for complete search history.

(56) References Cited

U.S. PATENT DOCUMENTS

2013/0345199 A1* 12/2013 Fretz et al. ................ 514/217.04

OTHER PUBLICATIONS

C.R. González et al., 41 Journal of Molecular Endocrinology, 415-421 (2008).*
O. Gualillo et al., 29 Trends in Pharmacological Sciences, 398-401 (2008).*
H. Kirchner et al., 15 Nature Medicine, 741-745 (2009).*

* cited by examiner

*Primary Examiner* — Alexander R Pagano
(74) *Attorney, Agent, or Firm* — Elizabeth A. Dingess-Hammond

(57) ABSTRACT

The present invention provides novel GOAT inhibitors and their salts and pharmaceutical compositions thereof.

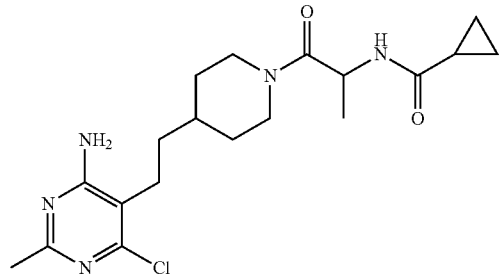

18 Claims, No Drawings

GHRELIN O-ACYL TRANSFERASE INHIBITOR

The present invention relates to a compound useful for inhibiting ghrelin O-acyl transferase (GOAT), pharmaceutical compositions and methods for treating diseases related to GOAT activity.

GOAT belongs to the membrane-bound O-acyl transferase (MBOAT) family of enzymes. It converts desacyl-ghrelin (also known as unacylated ghrelin or UAG) to a biologically active form, acyl-ghrelin (AG), by transferring a fatty acid to the Ser3 residue of the desacylghrelin peptide. Acyl-ghrelin has been shown to increase food intake and increase adiposity in humans and in rodents. Infusion of AG in humans has also been shown to suppress glucose-induced insulin secretion. Elimination of the ghrelin gene has been shown to enhance insulin release to prevent or ameliorate glucose intolerance in high-fat diet fed ob/ob mice.

The prevalence of obesity and diabetes coupled with the variable effectiveness and responses to current treatments for obesity and diabetes necessitate that more treatment choices be available to patients. A GOAT inhibitor is believed to be a useful agent in the treatment of obesity. It is further believed that a GOAT inhibitor may also be useful in reducing weight gain or weight regain as an adjunct to diet and/or exercise, other therapeutic medicinal agents or procedures designed to reducing weight gain or treat obesity. Similarly, a GOAT inhibitor may be useful in treating type 2 diabetes, singly or in combination with other treatments for type 2 diabetes.

The present invention provides a compound that is a GOAT inhibitor. In particular, the present invention provides a compound of formula

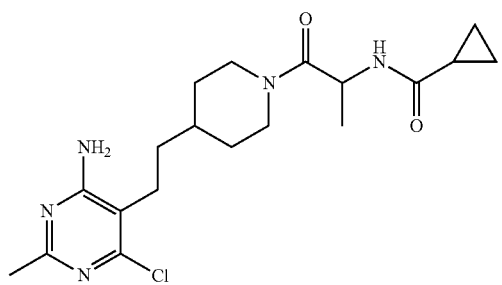 [SMILES: Cc1nc(N)c(CCC2CCN(C(=O)C(C)NC(=O)C3CC3)CC2)c(Cl)n1]

or a pharmaceutically acceptable salt thereof.

The present invention further provides a compound that is a GOAT inhibitor of formula

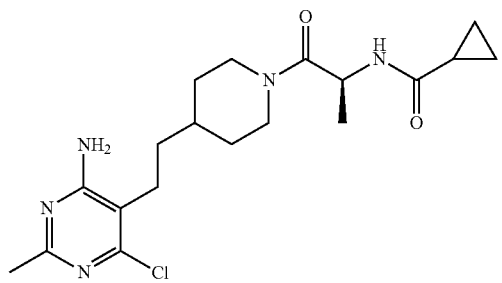 [SMILES: Cc1nc(N)c(CCC2CCN(C(=O)[C@H](C)NC(=O)C3CC3)CC2)c(Cl)n1]

The present invention provides a pharmaceutical composition comprising a compound of the invention, or a pharmaceutically acceptable salt thereof, and one or more pharmaceutically acceptable carriers, diluents, or excipients. In a further embodiment, the present invention provides a pharmaceutical composition comprising a compound of the invention and one or more other therapeutic agents.

A further aspect of the present invention provides a method of reducing weight gain or weight regain or treating type 2 diabetes or obesity comprising administering a compound of the present invention, or a pharmaceutically acceptable salt thereof, to a patient in need thereof.

The present invention also provides a compound of the invention, or a pharmaceutically acceptable salt thereof, for use in therapy, in particular for reducing weight gain or weight regain or treating type 2 diabetes or obesity. Furthermore, the present invention provides the use of a compound of the invention, or a pharmaceutically acceptable salt thereof, in the manufacture of a medicament for reducing weight gain or weight regain or treating type 2 diabetes or obesity.

The compound of the present invention is generally effective over a wide dosage range. For example, dosages per day fall within the range of about 0.03 to about 150 mg/Kg of body weight. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The term "treating" (or "treat" or "treatment") as used herein refers to restraining, slowing, stopping, or reversing the progression or severity of an existing symptom, condition or disorder.

As used herein, the term "reducing weight gain" refers to diminishing the increase in weight of a patient. The term "reducing weight regain" refers to diminishing the increase in weight of a patient experiencing rebound in weight after weight loss. Weight regain may be due to a rebound effect following cessation of weight loss achieved via diet, exercise, behavior modification, or approved therapies. For avoidance of doubt weight gain or weight regain as used herein refers to weight gain or weight regain induced by food intake or eating habits and does not refer to non-food related weight gain such as build up of fluids, weight due to water retention, muscle mass, or inflammation.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, $2^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that the compound of the invention, or pharmaceutically acceptable salt thereof, are comprised of a core that contains at least one chiral center:

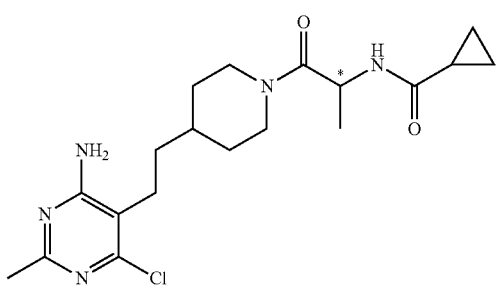 [SMILES: Cc1nc(N)c(CCC2CCN(C(=O)C(C)NC(=O)C3CC3)CC2)c(Cl)n1]

Although the present invention contemplates all individual enantiomers, as well as mixtures of the enantiomers of said compounds including racemates. the preferred compound of the invention is represented by the formula:

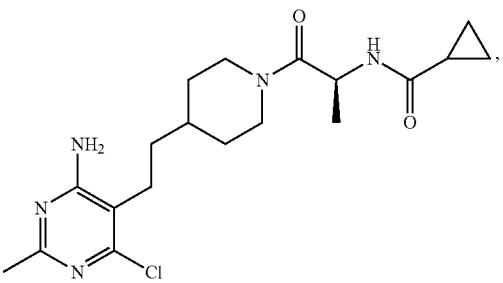 [SMILES: Cc1nc(N)c(CCC2CCN(C(=O)[C@H](C)NC(=O)C3CC3)CC2)c(Cl)n1]

or pharmaceutically acceptable salts thereof.

A compound of the present invention is preferably formulated as pharmaceutical compositions administered by a variety of routes. Such pharmaceutical compositions and processes for preparing the same are well known in the art. See, e.g., Remington: The Science and Practice of Pharmacy (A. Gennaro, et al., eds., 21st ed., Mack Publishing Co., 2005). More particularly preferred, is a pharmaceutical composition comprising a compound of the invention represented by the formula

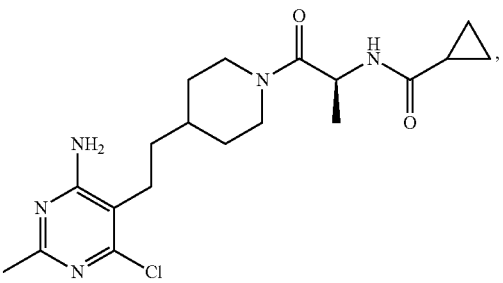 [SMILES: Cc1nc(N)c(CCC2CCN(C(=O)[C@H](C)NC(=O)C3CC3)CC2)c(Cl)n1]

or a pharmaceutically acceptable salt thereof and one or more pharmaceutically acceptable carriers or diluents.

Single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

It is well known in the art that agents for the treatment of diabetes and/or obesity may be combined with other agents for the treatment of diabetes and/or obesity. The compound of the invention, or a pharmaceutically acceptable salt thereof, may be co-administered, simultaneously or sequentially, with other effective treatment(s) for diabetes or obesity. The compound of the invention, or a pharmaceutically acceptable salt thereof, alone or in combination with other effective treatment(s) may be administered, simultaneously or sequentially, following approved medical procedures such as bariatric surgeries, for example, gastric bypass surgery or adjustable gastric banding procedures.

The present invention also encompasses intermediates and processes useful for the synthesis of the compound of the present invention.

Additionally, the intermediates described in the following schemes may contain a number of nitrogen protecting groups. The variable protecting group may be the same or different in each occurrence depending on the particular reaction conditions and the particular transformations to be performed. The protection and deprotection conditions are well known to the skilled artisan. See. e.g., Greene and Wuts, *Protective Groups in Organic Synthesis*, (T. Greene and P. Wuts, eds., 2d ed. 1991).

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R or S configuration of the compound of the invention may be determined by standard techniques such as X-ray analysis and correlation with chiral-HPLC retention time. The naming of the following Preparations and Example is generally performed using the IUPAC naming feature in MDL Accelrys® Draw version 4.0.NET.

As used herein, the following terms have the meanings indicated: "ACN" refers to acetonitrile; "BSA" refers to bovine serum albumin; "DCM" refers to dichloromethane; "DIPEA" refers to N,N-diisopropylethylamine; "DMF" refers to dimethylformamide; "DMSO" refers to dimethylsulfoxide; "EDTA" refers to ethylenediaminetetraacetic acid; "EtOAc" refers to ethyl acetate; "EtOH" refers to ethanol; "FBS" refers to fetal bovine serum; "HRP" refers to horseradish peroxidase; "IC50" refers to the concentration of an agent which produces 50% of the maximal response; "IPA" refers to isopropyl alcohol; "MeOH" refers to methanol; "MTBE" refers to methyl tert-butyl ether; "PBS" refers to phosphate buffered saline; "RT" refers to room temperature; "TEA" refers to triethylamine; "TFA" refers to trifluoroacetic acid; "$T_R$" refers to time of retention; "THF" refers to tetrahydrofuran; and "TMB" refers to 3,3',5,5'-tetramethylbenzidine.

LC-MS conditions (low pH): column: Phenomenex Gemini NX C18 2.1×50 mm 3.0 m; gradient: 5-100% B in 3 min, then 100% B for 0.75 min column temperature: 50° C.+/−10° C.; flow rate: 1 mL/min; Solvent A: deionized water with 0.1% formic acid; Solvent B: ACN with 0.1% formic acid.

Preparation 1

6-Chloro-2-methylpyrimidin-4-amine

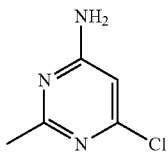

Charge a 5 L steel pressure vessel (autoclave) with 4,6-dichloro-2-methylpyrimidine (400 g, 2.45 mol) and ammonium hydroxide (2.8 L) at RT. Heat the reaction to 90° C. for 5 h. Cool the reaction mixture to RT and then filter the solid through a Buchner funnel. Wash the filtercake with water (200 mL) and hexane (200 mL) and then dry under vacuum to afford the title compound as a white solid (290 g, 82%). LC-ES/MS m/z 144.0 (M+1).

Preparation 2

6-Chloro-5-iodo-2-methylpyrimidin-4-amine

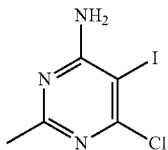

Combine 6-chloro-2-methylpyrimidin-4-amine (708 g, 4.93 mol) and MeOH (7.08 L) in a 20 L round bottom flask equipped with a mechanical stirrer. Cool to 0-5° C. Add iodine monochloride (4.806 kg, 29.6 mol) dissolved in MeOH (6 L) using an addition funnel over a period of 1 h. Warm the reaction mixture to RT and stir at RT for 16 h. Cool the reaction mixture to 0-5° C. and add sodium sulfite (46 L, 20% aqueous solution). Filter the resulting solid and wash with water (2 L) followed by hexane (3 L). Dry the solid under vacuum to afford the title compound as a white solid (1061 g, 80%). LC-ES/MS m/z 269.9 (M+1).

Preparation 3 tert-Butyl 4-[2-(4-amino-6-chloro-2-methyl-pyrimidin-5-yl)ethynyl]piperidine-1-carboxylate

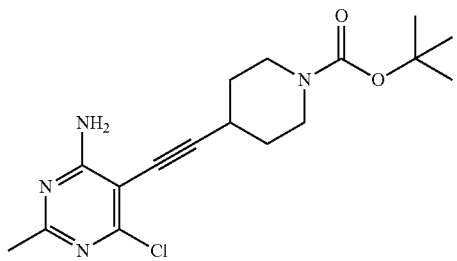 [SMILES: Cc1nc(N)c(C#CC2CCN(C(=O)OC(C)(C)C)CC2)c(Cl)n1]

Dissolve 6-chloro-5-iodo-2-methyl-pyrimidin-4-amine (20 g, 74.22 mmol), 4-ethynyl-piperidine-1-carboxylic acid tert-butyl ester (18.64 g, 89.06 mmol), and diisopropylamine (10.44 mL, 74.22 mmol) in THF (200 mL) in a 3-neck flask. Alternately evacuate and charge the flask with nitrogen 3 times. Add bis(triphenylphosphine)palladium(II) chloride (2.63 g, 3.71 mmol) and copper(I) iodide (0.713 g, 3.71 mmol) to the solution. Heat the mixture to between 50 to 55° C. for 16 h. Cool the mixture to RT and add more bis(triphenylphosphine)palladium(II) chloride (1.31 g, 1.86 mmol), copper(I) iodide (0.356 g, 1.86 mmol) and 4-ethynyl-piperidine-1-carboxylic acid tert-butyl ester (1.55 g, 7.42 mmol). Heat the mixture to 60° C. for 3.5 h. Cool the mixture to RT and concentrate under reduced pressure. Dilute the material with DCM (300 mL) and wash with saturated aqueous ammonium chloride solution (100 mL), water (100 mL), and saturated aqueous sodium chloride (100 mL). Dry the solution over MgSO$_4$, filter, and concentrate under reduced pressure. Purify the residue using silica gel chromatography (800 g silica gel column) eluting with 20% to 100% EtOAc in hexanes. Concentrate the purified fractions to give the title compound as a pale orange powder (22.6 g, 86%). LC-ES/MS m/z ($^{35}$Cl/$^{37}$Cl) 351.2/353.1 (M+1).

Preparation 4 tert-Butyl 4-[2-(4-amino-6-chloro-2-methyl-pyrimidin-5-yl)ethyl]piperidine-1-carboxylate

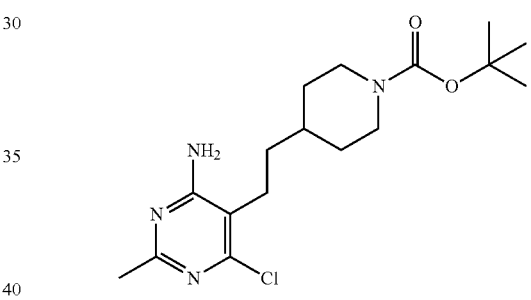

Combine tert-butyl 4-[2-(4-amino-6-chloro-2-methyl-pyrimidin-5-yl)ethynyl]piperidine-1-carboxylate (4.30 g, 12.26 mmol) and platinum(IV) oxide (0.139 g, 0.61 mmol) in EtOH (81 mL) and EtOAc (40 mL). Alternately evacuate and charge the flask with hydrogen using a hydrogen balloon and agitate at RT for 8 h. Monitor the reaction carefully so as to avoid a potential side product resulting from removal of the chloride in the molecule. Note that the product is more soluble in the solvent mixture than the starting alkyne. Filter the mixture through diatomaceous earth, rinsing with MeOH. Concentrate the solution under reduced pressure. Into the flask add silica, 1-propanethiol (4 g, loading=1.28 mmol/g, SILIABOND® Thiol from SILICYCLE®) (to remove residual palladium from the previous coupling reaction) and EtOAc (300 mL). Stir the material at RT 3 days. Filter the solids and concentrate the filtrate under reduced pressure. Repeat the hydrogenation on the resulting residue as follows. Charge the flask containing the residue with platinum(IV) oxide (0.139 g, 0.61 mmol), EtOH (81 mL) and EtOAc (40 mL). Alternately evacuate and charge the flask with hydrogen using a hydrogen balloon and agitate at RT for 8 h. Filter through diatomaceous earth, rinsing with MeOH, and concentrate the filtrate under reduced pressure. Repeat the hydrogenation on the resulting residue as follows. Charge the flask containing the residue with platinum(IV) oxide (0.139 g, 0.61 mmol), EtOH (81 mL) and EtOAc (40 mL). Alternately evacuate and charge the flask with hydrogen using a hydrogen balloon and agitate at RT for 8 h. Filter through diatomaceous earth, rinsing with MeOH. Concentrate the filtrate under reduced pressure onto silica gel (20 g). Purify the material using silica gel chromatography eluting with 70% to 100% EtOAc in hexanes (120 g column). Combine the purified fractions and concentrate under reduced pressure. Dilute the residue with DCM and hexanes and concentrate under reduced pressure three times. Place the material under vacuum to give the title compound as a white solid (3.20 g, 73%). LC-ES/MS m/z ($^{35}$Cl/$^{37}$Cl) 355.2/357.2 (M+1).

Preparation 5

6-Chloro-2-methyl-5-[2-(4-piperidyl)ethyl]pyrimidin-4-amine, hydrochloride salt

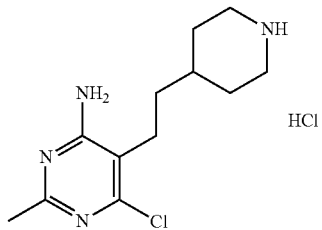 [SMILES: Cc1nc(N)c(CCC2CCNCC2)c(Cl)n1 ; Cl]

Dissolve tert-butyl 4-[2-(4-amino-6-chloro-2-methyl-pyrimidin-5-yl)ethyl]piperidine-1-carboxylate (29.00 g, 81.72 mmol) in 1,4-dioxane (145 mL) and add 4M hydrogen chloride in 1,4-dioxane (204.2 mL, 817.1 mmol). Stir the solution for 18 h at RT. Concentrate the mixture under reduced pressure, slurry in diethyl ether (250 mL), filter, and dry the resultant solid under vacuum to give the title compound as a crude white solid (29 g). LC-ES/MS m/z ($^{35}$Cl/$^{37}$Cl) 255.2/257.2 (M+1).

Alternate route for 6-chloro-2-methyl-5-[2-(4-piperidyl)ethyl]pyrimidin-4-amine (Preparations 6-10)

Preparation 6 tert-Butyl 4-(2-methylsulfonyloxyethyl)piperidine-1-carboxylate

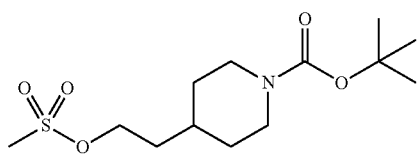 [SMILES: CC(C)(C)OC(=O)N1CCC(CCOS(C)(=O)=O)CC1]

Combine tert-butyl 4-(2-hydroxyethyl)piperidine-1-carboxylate (4.720 kg, 20.6 mol) with DCM (40 L) and TEA (3020 mL, 21.63 mol) in a 50 L reactor under a nitrogen atmosphere. Cool the solution to about 0° C. and slowly add methane sulfonyl chloride (2.478 kg, 21.63 mol) in DCM (5 L) while keeping the reaction temperature below 10° C. After the addition is complete stir the mixture for 18 h at 15° C. at which time TLC (1:1, hexane:EtOAc) shows no starting material remaining Wash the mixture with water (30 L) and allow the phases to separate. Concentrate the organic phase to a solid. Slurry the solid in MTBE (6 L), collect by filtration, and dry in a vacuum oven at 50° C. to provide the title compound as a white solid (5.67 kg, 91%).

Preparation 7 tert-Butyl 4-(3-cyano-4-ethoxy-4-oxo-butyl)piperidine-1-carboxylate

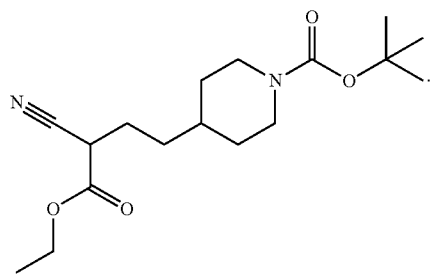 [SMILES: CCOC(=O)C(C#N)CCC1CCN(C(=O)OC(C)(C)C)CC1]

Combine tert-butyl 4-(2-methylsulfonyloxyethyl)piperidine-1-carboxylate (5.26 kg, 17.1 mol), ethyl cyanoacetate (7 kg, 62 mol), 21% sodium ethoxide in EtOH (8.25 L, 24.75 mol) and EtOH (35 L) in a 50 L reactor under a nitrogen atmosphere. Heat the mixture at 35-40° C. for 18 h at which time NMR analysis shows 20% of the mesylate remaining Continue heating the mixture at 35-40° C. for 24 h at which time NMR analysis shows only a small amount of mesylate. Slowly cool the reaction to RT and add glacial acetic acid (1422 mL, 22.68 mol) over 30 min. Concentrate the mixture using vacuum distillation and then partition between water (25 L) and EtOAc (35 L). Separate the layers and extract the aqueous phase with EtOAc (10 L). Combine the organic portions, wash with brine (15 L), and concentrate to a red oil. Purify the oil using silica gel chromatography (75 kg silica gel, 65-250 mesh), eluting with hexane (40 L) and then 20% EtOAc/hexane to provide a fraction (7.8 kg) that is 30% ethyl cyanoacetate/70% desired product. Concentrate the material by wipe film distillation at 100° C. and 210 mtorr vacuum, collecting the non-volatile fraction to provide the title compound (4.54 kg, 82%).

Preparation 8 tert-Butyl 4-[2-(4-amino-6-hydroxy-2-methyl-pyrimidin-5-yl)ethyl]piperidine-1-carboxylate

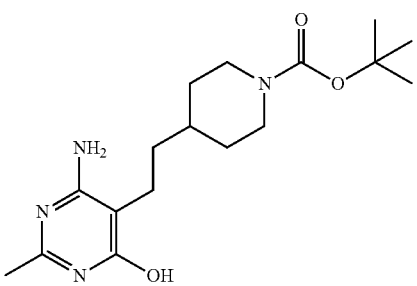 [SMILES: Cc1nc(N)c(CCC2CCN(C(=O)OC(C)(C)C)CC2)c(O)n1]

Combine tert-butyl 4-(3-cyano-4-ethoxy-4-oxo-butyl)piperidine-1-carboxylate (2.18 kg, 6.73 mol), acetamidine hydrochloride (1.27 kg, 13.46 mol, 95% assay) [Note: pre-dry the acetamidine hydrochloride by slurrying twice in toluene (10 L) and then stripping to dryness under vacuum], 21% sodium ethoxide in EtOH (6.73 L, 20.19 mol) and EtOH (10 L) in a 22 L reactor under a nitrogen atmosphere. Heat the reaction at reflux for 42 h. Adjust the reaction to about pH=5 with glacial acetic acid (1.2 L, 20.86 mol). Remove the EtOH by vacuum distillation on a rotary evaporator. Slurry the resulting solids in water (6 L), and then collect the solids by filtration, washing with additional water (2 L). Dry the solids in a vacuum oven at 50° C. to provide the title compound (1.72 kg, 76%). $^1$H NMR (500 MHz, CD$_3$OD) δ 4.83 (s, 3H); 4.05 (d, 2H), 2.75 (bs, 2H), 2.39 (m, 2H), 2.22 (s, 3H), 1.78 (d, 2H), 1.43 (m, 1H) 1.42 (s, 9H), 1.40 (m, 2H), 1.38 (m, 2H). Repeat the process, essentially as described, using tert-butyl 4-(3-cyano-4-ethoxy-4-oxo-butyl)piperidine-1-carboxylate (2.36 kg) to obtain the titled compound (2.01 kg, 82%).

Preparation 9

6-Amino-2-methyl-5-[2-(4-piperidyl)ethyl]pyrimidin-4-ol, dihydrochloride salt

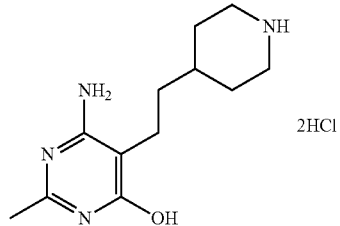 [SMILES: Cc1nc(N)c(CCC2CCNCC2)c(O)n1]

Combine tert-butyl 4-[2-(4-amino-6-hydroxy-2-methyl-pyrimidin-5-yl)ethyl]piperidine-1-carboxylate (3.73 kg, 11.09 mol) and IPA in a 50 L reactor under a nitrogen atmosphere. Add 12 N hydrochloric acid (3.05 L, 36.6 mol) with stiffing over 3 h. Heat the mixture at 50° C. for 16 h, forming a thick slurry. At that time NMR analysis shows no BOC group remaining. Cool the reaction mixture to 20-25° C., diluting with THF (12 L). Collect the solids by filtration. The filtration is slow and may take over 24 h to complete. Wash with IPA (2×10 L). Dry the material in a vacuum oven at 50° C. to provide the title compound (3.117 kg, 91%).

Preparation 10

6-Chloro-2-methyl-5-[2-(4-piperidyl)ethyl]pyrimidin-4-amine, dihydrochloride salt

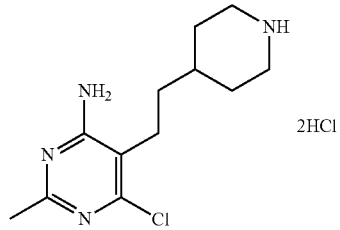 [SMILES: Cc1nc(N)c(CCC2CCNCC2)c(Cl)n1]

Combine 6-amino-2-methyl-5-[2-(4-piperidyl)ethyl]pyrimidin-4-ol, dihydrochloride salt (3.167 kg, 10.2 mol) and phosphorous oxychloride (30 L, 300 mol) under a nitrogen atmosphere in a 50 L reactor which is vented through a caustic (10% NaOH) scrubber. Add 85% phosphoric acid (1 L, 8.5 mol) to the stirred slurry. Heat the mixture slowly using a reactor jacket temperature of 75° C. At about 55° C., when off-gassing occurs, cool the scrubber in an ice water bath. When the off-gassing is slowed, heat the mixture at 90-95° C. for 50 h at which time TLC and NMR analysis shows the reaction to be complete. Remove the bulk of the excess phosphorous oxychloride by vacuum distillation (22 in Hg vacuum and 60° C. internal temperature) to recover 20 L in the distillate. Cool the mixture to 20-25° C. and then dilute with toluene (10 L). Further cool the mixture to <15° C. and slowly quench with water (1 L) keeping the temperature <30° C. After the toluene addition the mixture becomes very thick and difficult to agitate with the product phase remaining at the bottom of the reactor as a viscous semi-solid. Elevate the agitator blades in order to achieve any mixing. Add EtOH (10 L) to the mixture and stir for about 18 h at 25° C. At this point the viscous semi-solids are not yet completely digested, but are softened so that they can be manually probed. Agitate vigorously for another 4-5 h to completely digest. Cool the resulting slurry to 5-10° C. and collect the solids by filtration, washing with MTBE (8 L) to obtain wet product (about 6 kg).

Recrystillize the crude product by dissolving the wet cake in MeOH (35 L) at 40° C. Concentrate the solution by vacuum distillation, removing 15 L of solvent. Add IPA (35 L) and concentrate the slurry by vacuum distillation to remove 13 L of solvent. Cool the slurry to 5-10° C. and then filter the solids, washing with IPA (2 L), and then MTBE (8 L). Dry the solids in a vacuum oven at 55° C. to afford the title compound as an off-white solid (2.77 kg, 82%). Analytical calculated for $C_{12}H_{21}Cl_3N_4$: C, 43.98; H, 6.46; Cl, 32.46; N, 17.10. Found: C, 43.63; H, 6.53; Cl, 32.16; N, 16.86.

Preparation 11 tert-Butyl N-[(1S)-2-[4-[2-(4-amino-6-chloro-2-methyl-pyrimidin-5-yl)ethyl]-1-piperidyl]-1-methyl-2-oxo-ethyl]carbamate

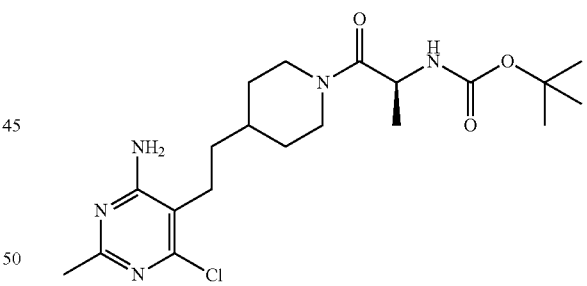

Into each of two round bottom flasks add 6-chloro-2-methyl-5-[2-(4-piperidyl)ethyl]pyrimidin-4-amine hydrochloride (12.50 g, 42.92 mmol), diisopropylethylamine (22.46 mL, 128.7 mmol) and DMF (100 mL). Cool the two mixtures in a cold water bath and stir for 5 min. Add to each of the mixtures [dimethylamino(triazolo[4,5-b]pyridin-3-yloxy)methylene]-dimethyl-ammonium hexafluorophosphate (17.95 g, 47.21 mmol) and (2S)-2-(tert-butoxycarbonylamino)propanoic acid (8.93 g, 47.21 mmol) in one portion. Stir the mixtures at RT for 90 min Pour the mixtures into separate separatory funnels along with water (300 mL) and EtOAc (400 mL), shake and partition. Extract the aqueous layers with EtOAc (3×300 mL), wash the respective organic layers with water (4×250 mL), saturated aqueous NaCl (200 mL) and dry over MgSO$_4$, filter and concentrate under reduced pressure. Purify the combined materials via silica gel chromatography eluting with 70% to 100% EtOAc in hexanes. Combine and concentrate the purified fractions under reduced pressure. Dilute the residue with EtOAc (500 mL) and wash with saturated aqueous $NH_4Cl$ (100 mL), saturated aqueous $NaHCO_3$ (100 mL), water (100 mL) and saturated aqueous NaCl (100 mL). Dry the organics over $MgSO_4$, filter, and concentrate under reduced pressure to give the title compound as a white solid (28.00 g, 76%). LC-ES/MS m/z ($^{35}Cl/^{37}Cl$) 426.2/428.2 (M+1).

Preparation 12

(2S)-2-Amino-1-[4-[2-(4-amino-6-chloro-2-methyl-pyrimidin-5-yl)ethyl]-1-piperidyl]propan-1-one

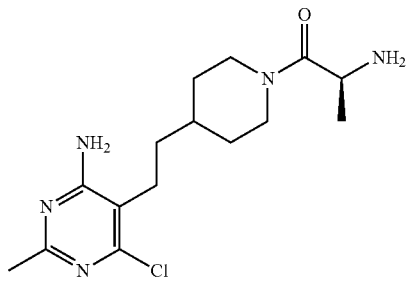 [SMILES: Cc1nc(N)c(CCC2CCN(C(=O)[C@H](C)N)CC2)c(Cl)n1]

Dissolve tert-butyl N-[(1S)-2-[4-[2-(4-amino-6-chloro-2-methyl-pyrimidin-5-yl)ethyl]-1-piperidyl]-1-methyl-2-oxo-ethyl]carbamate (15.78 g, 37.05 mmol) in DCM (185 mL), add TFA (185 mL) in a dropwise manner over 3 min, and stir overnight. Analyze the reaction by LCMS (low pH) to show complete conversion. Slowly add MeOH (400 mL) due to exothermic mixing. Prewash three SCX columns (50 g) with water (20 mL) and then MeOH (20 mL). Divide the reaction mixture into three equal portions and load equally onto the SCX columns Wash each column with water (40 mL) and MeOH (40 mL) collecting the washes in a vacuum flask. Elute the desired material from the SCX columns with 2 N ammonia in MeOH (60 mL) into a clean vessel. Combine the product containing solutions, concentrate under reduced pressure, azeotrope with DCM-hexanes (1:1), three times, and place under vacuum to obtain the title compound as a white foam (10.29 g, 84%). LC-ES/MS m/z ($^{35}Cl/^{37}Cl$) 326.2/328.2 (M+1).

Preparation 13

(2S)-2-Amino-1-[4-[2-(4-amino-6-chloro-2-methyl-pyrimidin-5-yl)ethyl]-1-piperidyl]propan-1-one hydrochloride salt

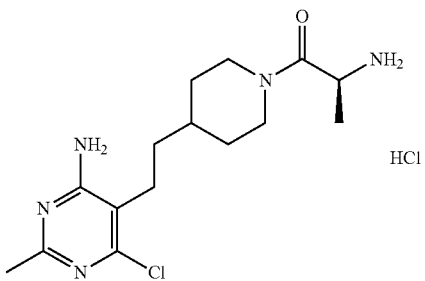 [SMILES: Cc1nc(N)c(CCC2CCN(C(=O)[C@H](C)N)CC2)c(Cl)n1 ; Cl]

Add tert-butyl N-[(1S)-2-[4-[2-(4-amino-6-chloro-2-methyl-pyrimidin-5-yl)ethyl]-1-piperidyl]-1-methyl-2-oxo-ethyl]carbamate (28.75 g, 67.49 mmol) to 1,4-dioxane (143.7 mL). Then add 4M hydrogen chloride in 1,4-dioxane (168.7 mL, 674.9 mmol) and stir for 10 min. Add MeOH (20 mL) and stir the mixture for 3 h with vigorous stirring. Concentrate the mixture under reduced pressure, dilute the solids with diethyl ether (200 mL), and stir overnight. Filter the material, rinsing with diethyl ether (2×25 mL). Dry the material via suction for 15 min, then place under vacuum for 1 h at 45° C. to obtain the title compound as a crude white powder (27.7 g). LC-ES/MS m/z ($^{35}Cl/^{37}Cl$) 326.1/328.2 (M+1).

Preparation 14

(2S)-2-Amino-1-[4-[2-(4-amino-6-chloro-2-methyl-pyrimidin-5-yl)ethyl]-1-piperidyl]propan-1-one, dihydrochloride salt

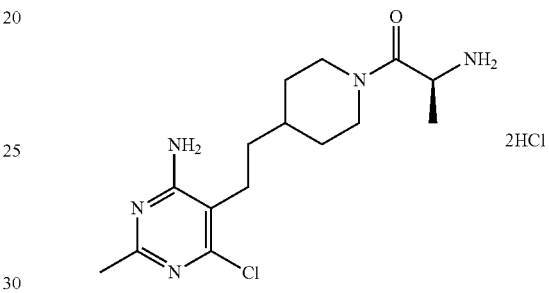

Heat IPA (154 mL) to 50° C. and add acetyl chloride (19.3 mL, 271 mmol) slowly due to an exothermic reaction. Stir the reaction at 50° C. for 10 min and then add tert-butyl N-[(1S)-2-[4-[2-(4-amino-6-chloro-2-methyl-pyrimidin-5-yl)ethyl]-1-piperidyl]-1-methyl-2-oxo-ethyl]carbamate (21.0 g, 45.3 mmol). Stir the reaction for 2 h monitoring via LCMS (low pH). Cool the reaction to RT and add diethyl ether (386 mL). Stir the slurry for 15 min. Filter the solids, washing with diethyl ether (2×50 mL) in a brisk manner as the material is hydroscopic. Filter the material and dry via filtration for 1 min, then in a vacuum drying oven at 50° C. overnight to give the title compound as a white powder (18.4 g). LC-ES/MS m/z ($^{35}Cl/^{37}Cl$) 326.1/328.2 (M+1). Counterion analysis by ion chromatography is consistent with the dihydrochloride salt.

Example 1

N-[(1S)-2-[4-[2-(4-Amino-6-chloro-2-methyl-pyrimidin-5-yl)ethyl]-1-piperidyl]-1-methyl-2-oxo-ethyl]cyclopropanecarboxamide

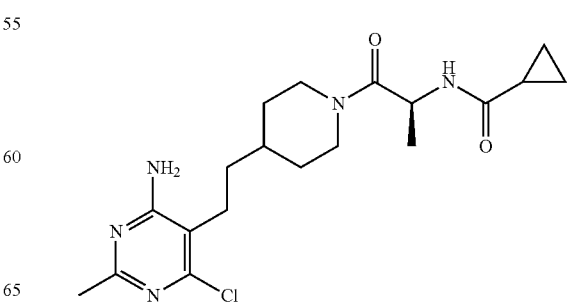

Add 1-hydroxy-7-azabenzotriazole (281 mg, 2.03 mmol) and 1-(3-dimethylaminopropyl)-3-ethylcarbodiimide hydrochloride (430 mg, 2.21 mmol) to a slurry of cyclopropanecarboxylic acid (161 µL, 2.03 mmol), (2S)-2-amino-1-[4-[2-(4-amino-6-chloro-2-methyl-pyrimidin-5-yl)ethyl]-1-piperidyl]propan-1-one (600 mg, 1.84 mmol) in anhydrous THF (12 mL). Then add TEA (770 µL, 5.52 mmol) and stir the resulting mixture at RT for 12 h. Dilute the reaction mixture with EtOAc (10 mL), filter over diatomaceous earth, and concentrate the filtrate in vacuo. Purify the resulting residue by mass-guided HPLC reverse phase chromatography (Agilent® 1200 LCMS and MSD mass spectrometer, 75×30 mm Phenomenex Gemini-NX®, 5µ particle size column with a 10×20 mm guard, 12-46% ACN in 10 mM aqueous ammonium bicarbonate solution, pH 10, gradient over 9 min) to obtain the title compound as a colorless glass (572 mg, 78%). LC-ESMS m/z ($^{35}$Cl/$^{37}$Cl) 394.2/396.2 (M+H).

Alternate Procedure with 1-Propanephosphonic Anhydride

Treat a mixture of (2S)-2-amino-1-[4-[2-(4-amino-6-chloro-2-methyl-pyrimidin-5-yl)ethyl]-1-piperidyl]propan-1-one, dihydrochloride salt (107.4 g, 183.15 mmol) in DCM (584 mL) with DIPEA (128 mL, 732.59 mmol). Cool the reaction mixture to 0° C. in an ice bath and add cyclopropanecarboxylic acid (21.8 mL, 274.72 mmol). Then add a solution of 1-propanephosphonic anhydride (50% solution in EtOAc, 174.8 g, 274.72 mmol) followed by additional DIPEA (40 mL) to render the reaction mixture basic. Stir at RT overnight. Wash the reaction mixture with water (1 L) and separate the layers. Dry the organic portion over MgSO$_4$ and concentrate in vacuo to obtain the crude product as an off-white foam. Purify the material by chromatography over silica gel (800 g, 0-10% MeOH in EtOAc). The appropriate fractions were combined with another batch of product (51 g) obtained by essentially following the same procedure using (2S)-2-amino-1-[4-[2-(4-amino-6-chloro-2-methyl-pyrimidin-5-yl)ethyl]-1-piperidyl]propan-1-one, dihydrochloride salt (77.9 g, 150.42 mmol). The combined lots were concentrated in vacuo to obtain a white solid (114 g). The product began to crystallize during the concentration. Triturate the material with hot EtOAc (200 mL), cool, and filter to obtain the title compound (111 g, 84%). LC-ES/MS m/z ($^{35}$Cl/$^{37}$Cl) 394.0/396.0 (M+1). Chiral analysis (OD-H column, 25% MeOH/iPrNH$_2$, 5.0 mL/min, 100 bar, 35° C., 220 nm) >99.9% ee; $T_R$=1.15 min.

GOAT is the principal enzyme that converts UAG to AG. For reviews of the role of GOAT and ghrelin see: Kristy M. Heppner et al, *The ghrelin O-acyltransferase-ghrelin system: a novel regulator of glucose metabolism*, Current Opinion in Endocrinology, Diabetes & Obesity 2011, 18:50-55; Phillip A. Cole et al., *Glucose and Weight Control in Mice with a Designed Ghrelin OAcyltransferase Inhibitor*, Science. 2010 Dec. 17; 330(6011): 1689-1692. doi:10.1126/science.1196154, Matthias H. Tschöp et al., *Gastric O-acyl transferase activates hunger signal to the brain*, Proc Natl Acad Sci USA. 2008 Apr. 29; 105(17): 6213-6214, and Jesus Gutierrez, et al., *Ghrelin octanoylation mediated by an orphan lipid transferase*, Proc Natl Acad Sci USA., 2008 Apr. 29, 105 (17): 6320-6325.

The role of GOAT is supported by the phenotypes observed in mice devoid of GOAT gene. Therefore, inhibition of GOAT is expected to decrease circulating AG and raise circulating UAG. Consequently, the ratio of AG to total ghrelin (UAG+AG) is reduced after GOAT inhibitor treatment.

In Vitro Cell Free Human GOAT Enzymatic Assay

Human GOAT gene (Accession number: NM_001100916) is subcloned to pAN51 baculoviral expression vector. Baculovirus stock is prepared following the Bac-to-Bac Protocol provided by the vendor, Invitrogen, California, USA. Five milliliters of human GOAT baculoviral stock are added to 500 mL Sf9 cells in HyQ SFX-Insect™ media (HyClone catalog number SH30278.02) at the density of 1×10$^6$ cells per milliliter in a 2 L Erlenmeyer flask. The flask with human GOAT gene infected Sf9 cells is put on a plate shaker at 120 rpm at 28° C. for 48 h. After 48 h incubation, cells are centrifuged at 1,000×g for 10 min at 4° C. The cell pellets are collected and stored at −80° C. in a freezer until ready for further processing.

Preparation of Microsomal Membrane of GOAT Enzyme for the Enzymatic Assay:

One gram cell pellets are suspended in 9 mL chilled homogenization buffer (50 mM Tris-HCl, 250 mM sucrose, adjusted to pH 7.5, and sterile filtered through 0.2 µm Millipore filter). The cell suspension is transferred to a Dounce glass homogenizer. Cell pellets are homogenized with 40 strokes on ice. The homogenate is centrifuged at 3,000 rpm in a Beckman swing bucket rotor at 4° C. for 10 min to remove unbroken cells. The supernatant is collected and centrifuged at 40,000×g for 1 h at 4° C. The resulting membrane pellet is suspended in the homogenization buffer using a Dounce glass homogenizer and stored at −20° C. in the freezer for the assay. For long term storage of the human GOAT enzyme membrane preparation, the suspended membrane is stored in a −80° C. freezer.

Human GOAT Enzymatic Assay Protocol:

Prepare test compounds in DMSO to make up a 0.2 mM stock solution. Serially dilute the stock solution in DMSO to obtain a ten-point dilution curve with final compound concentrations ranging from 10 µM to 0.5 nM in a 96-well round-bottom plate. Prepare enzyme and substrate solutions in assay buffer (0.02% Tween™-20 in 50 mM Tris, pH 7.5/250 mM sucrose/1 mg/mL BSA/10 mM EDTA). Add diluted compound (1 µL) to each well of row A to N of a corresponding low protein binding 384 well plate. Add human GOAT substrate mix (10 µL), consisting of human desacyl-ghrelin-biotin (CPC Scientific Inc., 6.0 µM final), octanoyl-CoA (Sigma, 60 µM final) and an AG specific antibody (WO 2006/091381) (1.0 µg/mL final), to the compounds. Add GOAT-His/sf9 enzyme preparation, that has been prepared in assay buffer (9 µL), to each well of the plate containing substrate and test compounds resulting in a final concentration of 0.01 µg/mL to initiate the reaction. Incubate the mixture for 1 h at RT on a gently rotating oscillator. Add 4 M guanidine hydrochloride (20 µL) to all wells, mix, and incubate for 3 h to stop the reaction.

Prepare ELISA plates (STREPTAVIDIN SPECTRAPLATE™ 384, Perkin Elmer) by blocking with 2% Heat-Inactivated FBS in PBS (40 µL) (Invitrogen) blocking buffer for 3 h. Aspirate the blocking buffer from ELISA plate and add blocking buffer (23 µL) to columns 1-24, rows A-N. Reserve rows O and P for the acylghrelin standard curve. Add the reaction mix (2 µL) to the ELISA plates. Prepare a 10 point standard curve (biotin-labeled octanoyl-ghrelin) by serial 2× dilution in blocking buffer containing 0.2M Guanidine hydrochloride starting at 2.5 pM. Incubate the reaction mixture or biotin-labeled AG standard in the ELISA plate overnight at 4° C. The following day, wash the plate 3× with wash buffer (0.1% Tween™-20/PBS, 100 µL per well in each wash cycle). Add AG specific antibody (WO 2006/091381) (25 µL of 0.5 µg/mL in blocking buffer) to each well and incubate at RT for 1 h. Wash the plate 3× with the wash buffer, similarly to the previous step. Add Protein G-HRP (25 µL) (Southern Biotech) diluted 3,000× in blocking buffer and incubate 1 h at RT. Wash the late 3× with wash buffer, as in the previous steps. Add TMB reagent (25 µL) (Kirkegaard & Perry Laboratories, Inc.) to each well and let develop for 20 min and stop with 1 M phosphoric acid (25 µL per well). Read plates at 450 nm using an Envision Multilabel plate reader. AG levels are calculated versus a fitted standard curve and percent inhibition calculated. The 10-point inhibition curve is plotted and fitted with the four-parameter logistic equation to obtain $IC_{50}$ values using Activity Base (ver. 7.3.2.1).

Following a protocol essentially as described above, the compound of Example 1 displays an $IC_{50}$ of about 192 nM±73, (n=5). The data demonstrates that the compound of Example 1 inhibits purified GOAT enzyme activity in vitro.

Comparing the change in the ratio of AG to total ghrelin in the compound treated group and that of the vehicle treated group reflects the degree of GOAT enzyme inhibition in vivo, due to the dynamic processing of UAG to AG by the GOAT enzyme. In the in vivo pharmacodynamic studies herein, the levels of AG and UAG in plasma and stomach in the vehicle and compound treated groups are measured by ELISA specifically to these two analytes. The total ghrelin level of each sample is computed as the sum of AG and UAG by these ELISA measurements. The ratio of AG to total ghrelin is defined by the level of AG in each sample divided by the level of total ghrelin in the same sample. The levels of AG, UAG and ratio of AG to total ghrelin in the vehicle treated group is computed and set as 100%. The relative change of these parameters in the compound treated group is then computed to determine the effectiveness of the test compound.

In Vivo Dose Dependent 3 Day BID Study for GOAT Inhibitor

Animals and Treatment:

Purchase male C57BL/6 mice from Harlan (Indianapolis, Ind.) at 9 weeks of age. House the mice individually in a temperature-controlled (24° C.) facility with a 12 h light/dark cycle (lights on 2200 h), and allow free access to a standard rodent chow (diet 2014, Harlan) and water. Typically, use the mice when they are 10-13 weeks of age at the time of the study. On day 0 of the experiment, randomize the mice into treatment groups (N=7/group) so each group has similar mean body weights. On day 1 and day 2, treat the animals with vehicle (1% hydroxyethylcellulose, 0.25% Tween 80, 0.05% antifoam) or test compound prepared in the vehicle as suspension at various dosages by oral gavage at 7 am and 7 pm. On day 3, fast the animals, move them into clean cages and dose with vehicle or the test compound again at 8 am by oral gavage. That same day at 1 pm, sacrifice the animals by decapitation to collect blood. For details of blood collection and plasma treatments see Blood collection and Extraction of Ghrelin from Plasma section below.

Blood Collection:

Collect approximately 600 µL blood into a pre-weighed EDTA tube containing 600 µL (defined as $V_{preservative}$) freshly-prepared preservative (4 mM PEFABLOC® [4-(2-aminoethyl) benzenesulfonyl fluoride hydrochloride], 72 mM NaCl, 58 mM NaF, 0.032 N hydrochloric acid, pH 3.0) and mix immediately. Weigh the tube again and keep on ice. To accurately determine the exact blood volume of each sample using this blood collection procedure, the weight of the blood for each mouse is computed using the following equation:

Weight of Blood=(Weight of the tube containing Blood+preservative)−(Weight of the tube containing preservative)

Blood volume($V_{blood}$)=(Weight of blood)/1.06

Note, the density of rodent blood is assumed as 1.06 g/mL.

Within 15 minutes after the blood collection, samples are centrifuged at 5000 rpm at 4° C. for 8 min Remove plasma (650 µL) to a 5 mL glass tube containing 1 N hydrochloric acid (65 µL), mix and keep on ice.

Ghrelin Extraction by SEP-PAK® Column:

AG and UAG are extracted from plasma using SEP-PAK®_$C_{18}$ column to remove interference prior to performing the ELISA. The solid phase extraction of AG and UAG peptides by SEP-PAK®_$C_{18}$ columns can be performed on a vacuum manifold (Waters Corp) or using a peristaltic pump. The sample SEP-PAK®_column extraction procedure is independently applied to the plasma sample obtained from each individual mouse. The general extraction protocol is described as follows.

All solutions used for the entire protocol of the SEP-PAK® column extraction should be at ice cold condition. Wet SEP-PAK®_columns (WAT054960, Waters Corp, Milford Mass.) with 99.9% ACN/0.1% TFA (1 mL of solution of 100 mL ACN/0.1 mL TFA). Apply pressure to adjust the flow-rate to about 1 mL/min to remove liquid from the column bed but do not allow the column to dry out at any point. Once liquid is removed from the column, stop the pressure. Equilibrate the columns with 3% ACN/0.1% TFA (1 mL of 97 mL water, 3 mL ACN, 0.1 mL TFA). Apply pressure to adjust the flow-rate to about 1 mL/min to remove liquid from the column bed, but do not let the column dry out. Dilute approximately 650 µL acidified plasma (defined as $V_{plasma\ added\ to\ column}$) to 1.4 mL ice cold 0.1% TFA. Load all diluted acidified plasma from the previous step onto the columns. Apply pressure to adjust the flow-rate to about 0.5 mL/min to allow sample passing through the column and ghrelin peptides to absorb onto the resin of the column Do not let the column dry out. Wash with 3% ACN/0.1% TFA (0.9 mL of 97 mL water, 3 mL ACN, 0.1 mL TFA). Apply pressure to adjust the flow-rate to about 1 mL/min to remove liquid from the column bed but do not let the column dry out. Repeat the wash two more times. Elute with 60% ACN/0.1% TFA (1 mL of 40 mL water, 60 mL ACN, 0.1 mL TFA). Put a collection tube underneath of each column, apply pressure to adjust the flow-rate to about 0.5 mL/min to push liquid through the column and collect the eluent into the collection tube. Freeze the samples on dry ice immediately. Lyophilize the samples in a speed-vac (Model# SC110A, Savant) and store at −20° C. until the ELISA assay is performed.

ELISA Assay for Ghrelin:

Coat 96-well MULTI-ARRAY® MSD® plates (Meso Scale Discovery, Gaithersberg, Md., Catalog # L15XA-3) with 100 µL of 1 µg/mL of an antibody (WO 2005/026211 AND WO2006/019577) that recognizes the mid-domain of both the acyl and unacylated forms of ghrelin in PBS (Invitrogen). Tap the sides of the plates to ensure coverage of wells, seal with adhesive plate sealer, and incubate overnight at RT. Discard the contents and add Blocker™ Casein in PBS (25 µL) (Thermo Scientific, Rockford, Ill., Catalog #37528) to each well. Reseal the plates and put on a plate shaker at RT for 1 h.

Reconstitute the lyophilized preserved plasma samples from the SEP-PAK® $C_{18}$ column extraction in Blocker™ Casein in PBS (400 µL to each sample, this volume is defined as $V_{reconsitution}$), mix well with a vortex mixer and incubate on ice for 45-60 min Discard the contents from the plates and add reconstituted plasma samples at 25 µL to each well. Prepare acylghrelin and unacylated ghrelin standard curves beginning with 8000 pg/mL and performing serial 1:4 dilutions for 8 total concentrations. Add the prepared standards in duplicate to the blocked plates with 25 μL in each well. Seal the plates and incubate at RT on a plate shaker for 2 h.

Discard the plate contents and wash three times with PBS including 0.1% Tween™ 20 (150 μL) (PBS-T). Acylghrelin specific antibody (WO 2006/091381) or unacylated ghrelin specific antibody (WO 2006/055347) labeled with MSD SULFO-TAG™ (Meso Scale Discovery) are diluted to 0.05 μg/mL in 0.2× Blocker Casein containing 0.05% Tween™ 20, named secondary antibody solution. Remove the final wash and add secondary antibody solution (25 μL to each well) which specifically recognizes AG or UAG. The plates are resealed and incubated for 1 h at RT on a plate shaker before finally washing 3× again with PBS-T (150 μL/well).

Discard the final wash and replace with 1×MSD Read Buffer (150 μL/well). Read the electrochemiluminescent signal generated by activation of the bound MSD SULFO-TAG™ label to the electrodes on the plates using the MSD® SECTOR® Imager 6000 analyzer (Meso Scale Discovery). Calculate concentrations of acylghrelin or unacylated ghrelin based on the respective standard curve generated by the MSD® software. Determine the actual plasma concentration for each sample by multiplying the measured acylghrelin or unacylated ghrelin level by a dilution factor. The dilution factor for each plasma sample is computed with the following equation.

$$DilutionFactor = \left(\frac{V_{blood} + V_{preservative}}{V_{blood}}\right) \times \left(\frac{V_{reconstitution}}{V_{plasma\ loaded\ to\ column}}\right)$$

Results:

Administration of the compound of Example 2 for 3 days decreases plasma AG by −1%, 5%, 45%, and 48%, and increases UAG by 2.24, 2.82, 2.53, and 2.89 fold, respectively at 0.3, 1, 3, and 10 mg/kg (results tabulated below). Administration at 0.3, 1, 3, and 10 mg/kg results in 39, 54, 71 and 77% reduction respectively in AG to total ghrelin ratio when compared to the vehicle-treated control animals. These results demonstrate that the compound of Example 1 suppresses AG production and elevates the UAG in circulation, as shown in the GOAT knock-out mouse, in vivo.

| Treatment | AG (% of control) | UAG (% of vehicle control) | AG/Total-ghrelin (% of vehicle control) |
|---|---|---|---|
| Vehicle | 100 | 100 | 100 |
| 0.3 mg/kg | 101 ± 025 | 224 ± 035 | 61 ± 04 |
| 1 mg/kg | 95 ± 018 | 282 ± 045 | 46 ± 011 |
| 3 mg/kg | 55 ± 06 | 253 ± 031 | 29 ± 04 |
| 10 mg/kg | 52 ± 010 | 289 ± 044 | 23 ± 04 |

I claim:
1. A compound of formula

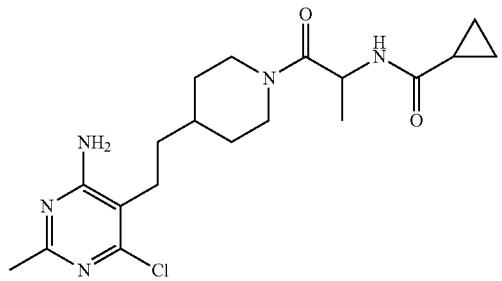

or a pharmaceutically acceptable salt thereof.

2. The compound of claim 1 of formula

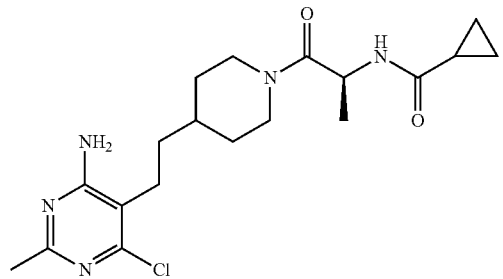

or a pharmaceutically acceptable salt thereof.

3. The compound of claim 2 of formula

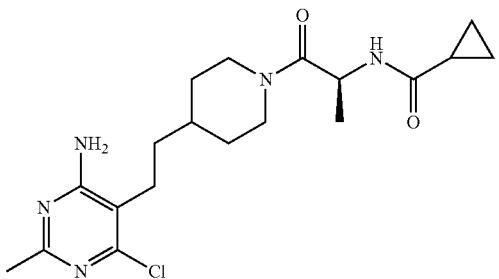 [SMILES: Cc1nc(N)c(CCC2CCN(C(=O)[C@H](C)NC(=O)C3CC3)CC2)c(Cl)n1]

4. A pharmaceutical composition comprising a compound of claim 1, or a pharmaceutically acceptable salt thereof, and one or more pharmaceutically acceptable carriers, diluents, or excipients.

5. A pharmaceutical composition comprising a compound of claim 2, or a pharmaceutically acceptable salt thereof, and one or more pharmaceutically acceptable carriers, diluents, or excipients.

6. A pharmaceutical composition comprising a compound of claim 3, or a pharmaceutically acceptable salt thereof, and one or more pharmaceutically acceptable carriers, diluents, or excipients.

7. A method of reducing weight gain comprising administering a compound according to claim 1, or a pharmaceutically acceptable salt thereof, to a patient in need thereof.

8. A method of reducing weight gain comprising administering a compound according to claim 2, or a pharmaceutically acceptable salt thereof, to a patient in need thereof.

9. A method of reducing weight gain comprising administering a compound according to claim 3, or a pharmaceutically acceptable salt thereof, to a patient in need thereof.

10. A method of reducing weight regain comprising administering a compound according to claim 1, or a pharmaceutically acceptable salt thereof, to a patient in need thereof.

11. A method of reducing weight regain comprising administering a compound according to claim 2, or a pharmaceutically acceptable salt thereof, to a patient in need thereof.

12. A method of reducing weight regain comprising administering a compound according to claim 3, or a pharmaceutically acceptable salt thereof, to a patient in need thereof.

13. A method of treating obesity comprising administering a compound according to claim 1, or a pharmaceutically acceptable salt thereof, to a patient in need thereof.

14. A method of treating obesity comprising administering a compound according to claim 2, or a pharmaceutically acceptable salt thereof, to a patient in need thereof.

15. A method of treating obesity comprising administering a compound according to claim 3, or a pharmaceutically acceptable salt thereof, to a patient in need thereof.

16. A method of treating type 2 diabetes comprising administering a compound according to claim 1, or a pharmaceutically acceptable salt thereof, to a patient in need thereof.

17. A method of treating type 2 diabetes comprising administering a compound according to claims 2, or a pharmaceutically acceptable salt thereof, to a patient in need thereof.

18. A method of treating type 2 diabetes comprising administering a compound according to claim 3, or a pharmaceutically acceptable salt thereof, to a patient in need thereof.

* * * * *